United States Patent [19]

Osbon

[11] Patent Number: 5,234,402
[45] Date of Patent: Aug. 10, 1993

[54] APPARATUS AND METHOD FOR AUGMENTING MALE POTENCY WITH USER TISSUE PROTECTION

[75] Inventor: James B. Osbon, Richmond, Va.
[73] Assignee: Osbon Medical Systems, Ltd., Augusta, Ga.
[21] Appl. No.: 899,554
[22] Filed: Jun. 16, 1992
[51] Int. Cl.$^5$ .............................................. A61F 5/41
[52] U.S. Cl. ............................................... 600/41
[58] Field of Search ............................ 600/38, 39, 41

[56] References Cited

U.S. PATENT DOCUMENTS

| | | |
|---|---|---|
| D. 317,50 | 6/1991 | Osbon . |
| D. 317,505 | 6/1991 | Osbon . |
| 1,133,958 | 3/1915 | Henderson . |
| 1,608,806 | 11/1926 | Nelson . |
| 3,455,301 | 7/1969 | Clark . |
| 3,621,840 | 11/1971 | Macchioni . |
| 3,705,580 | 12/1972 | Gauthier . |
| 3,759,253 | 9/1973 | Cray . |
| 4,240,413 | 12/1980 | Hanus . |
| 4,539,980 | 9/1985 | Chaney . |
| 4,641,638 | 2/1987 | Perry . |
| 4,724,829 | 2/1988 | Knapps . |
| 4,856,498 | 8/1989 | Osbon . |
| 4,856,534 | 8/1989 | Sorkin et al. . |

OTHER PUBLICATIONS

James E. Couch, PH.D.; Functional Human Anatomy; pp. 434, 436-437, 447-448; 1972; Great Britain.
Impotence Resolved; by Mission Pharmacal Company; 6 page brochure; no date; San Antonio, Texas.
Three brochures on "VED SofTouch Constriction Seal"; by Mission Pharmacal Company; 8 pages; no date; San Antonio, Texas.

*Primary Examiner*—Cary E. O'Connor
*Attorney, Agent, or Firm*—Dority & Manning

[57] ABSTRACT

Apparatus and method for augmenting male potency cinctures a vacuum induced engorged condition of a male sex organ while also protecting abdominal and scrotal tissue during application of vacuum force to the user. An elastic cincture band has an annular tissue shield secured thereto and preferably reinforced by integrally formed handles. The cincture band and handles are small enough to fit in the open receiving end of a vacuum erection chamber while the tissue shield is large and rigid enough to fit across the vacuum erection chamber open receiving end. The shield is received against the abdomen of a subject while the cincture band is received about the root of the subject's male sex organ and inside the vacuum erection chamber open end. In such position, the tissue shield is interposed between the user's abdomen and the vacuum erection chamber for protecting against abdominal or scrotal tissue (and the anatomy within the scrotum) being drawn into the vacuum chamber during therapy. Integral handles are secured to the cincture band and may be attached or unattached to the tissue shield. A urethra channel for improved discharge of seminal fluids and lateral dorsal venous process pressure points for enhancing the cincturing function may be included in the cincture band inside diameter.

39 Claims, 4 Drawing Sheets

APPARATUS AND METHOD FOR AUGMENTING MALE POTENCY WITH USER TISSUE PROTECTION

BACKGROUND OF THE INVENTION

The benefit of priority is hereby claimed under 35 U.S.C. Section 120, based on copending application U.S. Ser. No. 07/830,061, filed Feb. 3, 1992, for inventor James B. Osbon on an invention entitled "MALE ORGAN CONDITIONING APPLIANCE."

The present invention relates in general to improved apparatus and method for augmenting male potency and in particular to improved cincturing devices and methods which also provide improved comfort and safety during use of a vacuum erection chamber of the type having an open receiving end for receipt of a user's male sex organ.

Impotence, or sexual dysfunction, is a chronic and persistent problem among as much as 10 percent of the entire adult male population of the United States. Whether due to psychological or physical causes, impotence is the inability to achieve or maintain an adequate erection of the male sex organ, i.e., penis, for sexual intercourse.

The physical events of an erection are well known, and generally involve the inflow and retention of blood into certain cavernous bodies of the male sex organ so that it becomes stiff and erect, i.e., distended. As the stimulated condition subsides, natural processes cause (or permit) the blood to drain from the cavernous bodies of the penis and the penis again becomes flaccid.

The foregoing facts have resulted in efforts for many years to treat impotence through the use of various cincturing or tourniquet like devices. Generally speaking, such devices may typically comprise a circular element received about the male sex organ, such as at its base or root, for supplementing the natural forces which restrict the egress of blood from engorged penile cavities. Various elastic rings or the like are known for such purposes. See for example, Chaney (U.S. Pat. No. 4,539,980), which discloses a generally circular elastic ring with attached handles to function as a male organ conditioner by being applied to the root of a penis for securing an engorged condition thereof.

While such technology has addressed the problem of maintaining or securing a penile erection, another facet of the impotence problem which has been long addressed is the initial inducement or production of a suitable erection. For example, the above-referenced Chaney '980 patent suggests the use of a massaging action below or behind the scrotum to induce a forward blood flow into the penis, overcoming restrictive radially inward compressive forces of the elastic ring already applied to the base of the flaccid penis. In other words, it is intended that blood be manually massaged passed the elastic ring at the base of the penis with such ring then acting as a check valve.

Improvements to the foregoing apparatus and methodology for achieving (and sustaining) penile erection have been sought. One major alternative to the use of surgical treatments such as penile prosthetic implants or vascular reconstructive surgery, has been vacuum erection enhancement therapy. Vacuum erection device therapies operate on the principle that a suitable erection can be obtained by placing the user's penis into an open receiving end of a vacuum chamber or cylinder which then with vacuum force draws blood into the cavernous bodies of the penis. Once produced, the vacuum induced erection may be captured, i.e.. maintained, by use of cincturing devices as referenced above, for example elastic constriction rings.

While no form of medical treatment can ever be expected to be 100 percent effective, generally speaking, vacuum tumescence enhancement therapy is a favorable treatment for a number of reasons. For example, it will not interfere with other treatments, there are no permanent implants, it can be discontinued at any time, it is relatively inexpensive, and it is highly effective and carries a relatively high success rate.

One potentially negative aspect of the use of vacuum erection devices and such therapy is a natural consequence of the fact that human sexual organs are naturally highly sensitive regions of the body which could be harmed by improperly applied or excessive vacuum forces. For example, the penis is a highly vascular and sensitive organ which can respond differently to a given amount of vacuum force from one patient to another. One reason for this is simply due to the variety in specific sizes of the human anatomy, including differential variations between flaccid and erect states of the male sex organ, and other variables and factors which can limit optimum matching of the vacuum therapy equipment with a given patient's physical condition.

In addition to the sensitivity of the penis, interaction with the next physically adjacent sexual features is possible during vacuum erection therapy. More specifically, the scrotum is a pouch of relatively loose skin which projects from the lower part of the abdominal wall just below the base of the penis. The scrotum has two lateral portions for enclosing and respectively supporting in suspension the testes, generally oval organs averaging from about 4 to about 5 centimeters in length. The testes are essential male sex organs of reproduction which have the dual functions of producing spermatozoa and the male sex hormone testosterone. The spermatozoa are stored in a mass of coiled tubing referred to as the epididymis, which is also protectively received in the scrotum. Spermatozoa are forwarded from the epididymis to the ductus deferens, from which the sperm reach the ejaculatory duct and are expelled from the male sex organ through the urethra.

The significance of the foregoing physical anatomy is that such all important organs are received in suspension in the relatively loose folds of the skin comprising the scrotum. However, the proximity of the scrotal and other abdominal wall tissue or skin adjacent to the base of the penis brings such anatomy into close proximity with the open receiving end of a vacuum erection device applied to a user's penis. Therefore, there is the potential for highly undesirable intake of skin, i.e., scrotal or abdominal tissue, into the vacuum erection chamber during vacuum therapy. This scrotal tissue intake, depending on the degree or time extent thereof, is not necessarily harmful to the important sexual organs described above and contained in the scrotum, but certainly has the capacity to reduce the comfort level of the male subject. Given the nature of the therapy involved, and the frequent psychological implications of both the condition and the therapy selected, discomfort levels of the user could result in a disproportionate response level of anxiety or of loss or questioning of confidence in the therapy chosen, all of which is highly undesirable and at cross purposes to the overall therapy.

The considerable variety of devices previously available for the intended purpose of maintaining penile erections have considered a variety of attendant problems associated with the use of such devices. For example, the device must be applied to the user and in some fashion secured thereto (as well as subsequently removed therefrom). However, such devices have typically not acknowledged or addressed the specific problem of scrotal or abdominal tissue intake during vacuum erection therapy, especially since not all such devices are even intended for use in conjunction with such form of therapy, but many rather are intended to capture natural or manually produced erections.

Many prior art devices have typically comprised a generally circular or round securement member designed to be received at some point about the user's penis, typically at the base or root of the penis. Other elements or features have been secured to or project from such ring-like cincture element. Various functions have been performed by such features, such as providing structure or a base for attachment of the device to the user or to some other device, providing a structural foundation or strengthening for the device, performing hygienic purposes such as a disease shield, or performing purely mechanical functions such as serving as handles. Various examples of such prior art devices are disclosed in the following exemplary United States patents: Osbon, U.S. Pat. Nos. Des. 317,505 and Des. 317,504; Sorkin et al.. U.S. Pat. No. 4,856,534; Knapps, U.S. Pat. No. 4,724,829; Hanus. U.S. Pat. No. 4,240,413; Cray, U.S. Pat. No. 3,759,253; Gauthier, U.S. Pat. No. 3,705,580; Macchioni, U.S. Pat. No. 3,621,840; Clark, U.S. Pat. No. 3,455,301; Nelson. U.S. Pat. No. 1,608,806; and Henderson, U.S. Pat. No. 1,133,958.

Osbon (U.S. Pat. No. 4,856,498) commonly assigned with the subject application discloses a vacuum generating and constriction apparatus for augmenting male potency. Acknowledged therein is a scrotal tissue intake problem, i.e., the possibility of scrotal tissue being drawn up into a vacuum cylinder and causing user discomfort. The Osbon '498 patent proposes to address the tissue intake problem by providing adapter inserts of differing internal diameters to be selected and used in the open receiving end of the vacuum erection chamber. In other words, it is intended to reduce the number of physical conditions which could result in tissue intake by more closely matching the size of the vacuum structure inside diameter to the size of the outside diameter of the male sex organ anatomy involved. While effective to an extent with use of such structure, such approach does not avail patients who have vacuum erection chambers which are not designed to receive such adapter inserts, or whose physical anatomy is incompatible with being more closely matched by the use of adapter inserts to the chambers which they use.

The above-referenced Osbon '498 patent further discloses a therapeutic use of an additional or second vacuum step so as to partially increase penile engorgement after a constriction band has been placed on the base of an organ. As described therein, a constriction band such as shown in FIG. 4 of the '498 patent is elastic in nature and has specifically designed handle means which at rest remain in close relationship to the ring. After the ring is applied to the base of a male sex organ for capturing a certain level of induced engorgement thereof, the male sex organ is reintroduced (or introduced) into a vacuum chamber with both the ring and the particularly designed handles received inside the open receiving end of the vacuum chamber. Thereafter, an additional level of vacuum induced engorgement may be obtained with the constriction ring in place. Such supplemental or second vacuum step constitutes a second opportunity for the occurrence of scrotal tissue intake. Addressing such possibility once the penis is enlarged to a certain extent and in receipt of a constriction ring thereon could require the patient to change to an adapter insert of a different size (assuming that the patient has available in the first place a vacuum erection chamber with adapter insert features).

Perry (U.S. Pat. No. 4,641,638) discloses an alternative to use of an elastic member for cincturing an engorged penile condition. A prosthetic device of fixed outside diameter comprises a tubular sleeve element which is applied to the base of the male sex organ. An insertion device with a suction cup-like member may be attached to the tip of a flaccid male sex organ and used to draw the organ outward for reciprocation of the tubular element along the length of the penis to be seated at its base.

In the Perry device, the inside diameter of the tubular element includes an expandable diaphragm. The proximal end of the tubular device includes a flared flange portion through which passes an inlet opening which is in airflow communication with an internal generally annular air cavity defined between the expandable diaphragm and the fixed outside diameter of the tubular element. A flexible conduit connects to the opening at the base of the flared portion and further connects to an air pressure gauge, a check valve, and a hand pump mechanism. Once a sufficient amount of blood has entered the penis through normal physiological response, it is intended that the user throttle the valve accordingly and use the manual bulb pump to enlarge the expandable diaphragm (radially inward) and constrict the penis. However, it is instructed that before ejaculation during intercourse, the check valve must be manually manipulated to an open position so as to release the constriction of the expandable diaphragm and avoid the otherwise possibility of injury to the user.

The Perry patent describes an alternative to the natural erection process which involves an artificial vascularization comprising application of a vacuum chamber to the tubular member seated against the above-mentioned flared flange portion so as to supposedly eliminate air flow into the vacuum chamber from its open end. Once erection is obtained with the vacuum cylinder, the check valve and manual pump are again utilized to constrict the root of the penis. Likewise, again prior to ejaculation, the valve must be manipulated to release the constriction to otherwise prevent the occurrence of trauma during ejaculation due to natural physiologically increased vascularization of the penis just prior to ejaculation.

Whether relying on a natural physiological erection or an artificially induced erection, at all times the check valve and flexible tubing arrangement must remain in place and be attended to by the user in order for the Perry cincturing fixed outside diameter tubular member to function. Such operations clearly have the potential for interrupting normal intercourse activities and otherwise significantly detracting from the experience in comparison with a fully natural experience.

While the Perry arrangement makes use of a relatively nonelastic cincturing device intended for effecting a seal with an artificial vacuum erection chamber, there is apparently no specific acknowledgement or addressing of the need to protect sensitive surrounding tissue and organs. Another known device makes use of an elastic element for contributing to a seal with the vacuum chamber, but likewise apparently makes no specific acknowledgement of the potential problem of tissue vacuum intake. Specifically, the Mission Pharmacal Company of San Antonio, Tex. 78296, has marketed a penile constriction seal referred to under the name "SofTouch." Such constriction seal is described as having a central stem for restricting blood flow both to and from a user's penis and a flange for effecting a seal against a vacuum erection cylinder for the purpose of improving pump efficiency. The Mission Pharmacal Company constriction seal structure comprises a highly flexible simple annular flange of about 3.5 inches outside diameter with a central upright stem about 0.625 inches tall and having an inside diameter of only 0.375 inches (approximately the diameter of a pencil).

The Mission Pharmacal Company brochure materials describe two alternative approaches for seating the constriction seal about the base of the penis. One approach involves use of an applicator cone and annular applicator sleeve. Considerable and multiple applications of lubricant are made to the outside of the applicator cone and the inside of the seal stem. The flange is then used as handles to draw the elastic stem down around the applicator cone onto an associated applicator sleeve. The sleeve is then placed over the head of a penis in its flaccid or semi-flaccid state, and moved to the base of the penis, after which the seal is transferred from the sleeve onto the base of the penis. The flange portion is subsequently again used as handles for removal of the 0.375 inches diameter stem (unstretched measurement) from the penis.

The Mission Pharmacal Company brochures describe an alternative method of fitting the constriction seal onto the penis. The user is to insert the first two fingers of each hand into the 0.375 inch inside diameter stem and spread the opening of the stem. Continuing to hold the stem open, the flaccid or semi-flaccid penis is then to be inserted through the stem and the seal pulled against the base of the penis. Both the penis and the inside of the stem are to be lubricated prior to such seating efforts.

Aside from apparent difficulties in manipulation of the soft device with an initially relatively small inside diameter onto a user's penis, the Mission Pharmacal Company brochures also report clinical evaluations indicating a 43 percent negative rating as to whether the constriction seal provides a more effective seal for pumping. Such a highly negative rating would tend to indicate that such device does not provide an effective solution to the potential problem of tissue vacuum intake through use of an elastic device, which problem apparently is not expressly acknowledged by the Mission Pharmacal Company literature.

The complete disclosures of all of the above-referenced United States patents are fully incorporated herein by reference.

SUMMARY OF THE INVENTION

The present invention recognizes and addresses various of the foregoing problems, and others, concerning vacuum erection therapy. Thus, broadly speaking, a principal object of this invention is improved apparatus and methodology for augmenting male potency, particularly involving vacuum erection devices and therapies. More particularly, a main concern is improved apparatus and methodology for augmenting male potency while protecting abdominal and scrotal tissue (e.g., skin) and organs during vacuum erection therapy of a male subject.

Another general object of the present invention is advancement of vacuum erection therapy by reducing the occurrence and prospect for occurrence of user discomfort and/or injury. A more particular present object is to provide improved apparatus and methodology which provides the foregoing advancement in conjunction with an elastic penile erection constriction device so as to minimize artificial interruption of sexual activity and maximize duplication of natural experiences during such activity.

Still a further more particular object is to provide a constriction device which acknowledges and effectively addresses the above-mentioned matters of user comfort and safety, but which is also easy to use at all times (i.e., before, during, and after sexual intercourse) and highly effective in the function of maintaining engorgement or erection of the male sex organ.

In conjunction with providing such an improved constriction device, it is desired to provide a device which accommodates the alternate inclusion of various additional features. For example, it is desired to provide for the alternate inclusion of features which accommodate improved seminal discharge during climactic expulsion and which provide for improved specific restriction of blood egress so as to still further improve user comfort while wearing the present constriction device.

In addition to the foregoing, another object is to provide improved devices and methods which address the foregoing comfort and safety concerns which are also user friendly in the specific sense that they are relatively easy for the user to manipulate and position. Such improved manipulation is sought both in the initial application and subsequent removal of the device.

Additional objects and advantages of the invention are set forth in, or will be apparent to those of ordinary skill in the art from, the detailed description which follows. Also, it should be further appreciated that modifications and variations to the specifically illustrated and discussed features, materials, and steps hereof may be practiced in various embodiments and uses of this invention without departing from the spirit and scope thereof, by virtue of present reference thereto. Such variations may include, but are not limited to, substitution of equivalent means and features, materials, or steps for those shown or discussed, and the functional or positional reversal of various parts, features, steps, or the like.

Still further, it should be understood and recognized that different embodiments, as well as different presently preferred embodiments, of the subject invention may include various combinations or configurations of presently disclosed features, elements, or steps, or their equivalents (including combinations of features or steps, or configurations thereof not expressly shown in the figures or stated in the detailed description). One exemplary such embodiment of the present invention relates to an elastic penile erection constriction device for improved comfort and safety during use of a vacuum erection chamber having an open receiving end for receipt of a user's male sex organ, such end being formed with predetermined inside and outside diameters. Such device comprises in combination specific forms of elastic ring means, handles means, and flange means, all in accordance with the subject invention.

The foregoing exemplary elastic ring means preferably are functional for retaining an engorged condition of a user's male sex organ by restricting the outward flow of blood therefrom. Such elastic ring means have respective inside and outside diameters, including a predetermined inside diameter sized for initial receipt of the ring about the base of a user's male sex organ and a predetermined outside diameter sized for receipt of such ring means within the inside diameter of a vacuum erection chamber open receiving end.

The foregoing exemplary handle means are preferably associated with the elastic ring means and functional for user manipulation of the constriction device. Such handle means project from the ring means a predetermined distance sized for receipt of the handle means within the inside diameter of the above-referenced vacuum erection chamber open receiving end.

Still further, such exemplary flange means are associated with the elastic ring means and project radially outward therefrom a distance greater than the outside diameter of the vacuum erection chamber open receiving end so as to be functional for preventing the ingress of the user's scrotal and abdominal tissue (and organs received within the scrotum) into such receiving end during vacuum operations of the vacuum erection chamber whenever the constriction device is seated about the base of the user's male sex organ.

In specific embodiments, such flange means may preferably comprise a generally planar member which may be received on either one axial side of the ring means or at an intermediate position about its outside diameter. The handle means may be integrally formed with the flange means or separate therefrom, depending on given embodiments.

Still further, such an exemplary constriction device may alternatively include urethra channel means and/or enhanced pressure means. Such urethra channel means may be formed in the elastic ring means and be functional for receiving the urethra of the user's male sex organ for improved user seminal discharge during climactic expulsion. Exemplary enhanced pressure means may also be formed in the elastic ring means and be functional for relatively increasing radially inward pressure on the user's male sex organ at least at one circumferential location thereof.

Another present exemplary embodiment concerns an apparatus for cincturing an engorged condition of a user's penis for improved male potency and for protecting sensitive scrotal and abdominal tissue of the user during vacuum inducement of such penile engorged condition. Such apparatus preferably includes a particular cincture band of elastic material, a urethra cradle formed in such band, a pair of curved loop handles integrally formed with the band, and a scrotal and abdominal tissue shield also integrally formed with such band.

The above-referenced exemplary cincture band preferably has an inside diameter of generally about 0.7 to about 0.9 inches, a band wall thickness of generally about 0.08 to 0.12 inches, and a band axial thickness of about 0.35 to about 0.55 inches. The above-referenced urethra cradle may be formed in a radially outward direction in a predetermined circumferential location in the cincture band inside diameter. The cradle has a depth of generally at least about 0.05 inches for axial alignment with and receipt of the user's urethra whenever the cincture band is applied in a predetermined rotational relationship about the base of a user's penis.

The handles integrally formed with the cincture band project radially outward from such cincture band in opposite directions centered respectively about 90 degrees from the urethra cradle about the circumference of the band. Each handle projects radially outward preferably generally less than 1 inch from the center of the cincture band so that both the band and the handles may be received in an open end of a vacuum erection chamber having an open end inside diameter of generally at least about 2 inches.

The referenced scrotal and abdominal tissue shield preferably comprises a planar annular member integrally formed on one axial side of the cincture band so as to be received against the abdomen of a user whenever the cincture band is applied to the base of a user's penis. The annular member has an inside diameter generally co-extensive with that of the cincture band and an outside diameter generally concentric with the cincture band and generally at least about 3 inches in diameter. With such an arrangement the user's abdominal and scrotal tissue may be shielded from vacuum forces applied to the user's penis whenever an operating vacuum erection chamber is seated about a user's penis with the chamber open end pressed against the user's abdomen, with the tissue shield interposed between the user's abdomen and such chamber open end.

The foregoing apparatus may further include embodiments including combinations therewith of a vacuum chamber means for selectively inducing the above-referenced engorged condition of the user's penis.

Yet another construction comprising a present exemplary embodiment includes an improved cincturing device for augmenting male potency and protecting abdominal and scrotal tissue during vacuum erection therapy of a male subject. Such device preferably comprises an elastic cincture band to be received about the root of a subject's penis and having an unstretched inside diameter of at least generally about 0.75 inches so as to facilitate application of such band to a subject's penis which is in a less than fully erect state. Such device also further includes a generally planar tissue shield of generally elastic material having an annular opening corresponding to that of the band. The shield is attached to the band and is sufficiently large for extending radially outward from the band at least about 1.5 inches in all directions from the band center. The shield is also sufficiently rigid for preventing abdominal and scrotal tissue of a subject from being drawn into a vacuum erection chamber whenever an open end of such a chamber during its vacuum operation is applied to the shield with the shield received against the abdomen of a subject and with the band received about the root of the subject's penis and inside the vacuum erection chamber open end.

It is to be further understood that the subject invention includes methods and methodology corresponding with the above-discussed exemplary devices and apparatus. For example, one present method of augmenting the potency of a male subject with vacuum erection therapy while protecting abdominal and scrotal tissue of such male subject, in accordance with the subject invention, makes use of the just described improved cincturing device. Such a device is used per the present method in conjunction with a generally elongated vacuum erection chamber with an open end for receiving a subject's penis therethrough into the chamber and a vacuum source for controllably evacuating such chamber. The cincture band is applied to the base of the subject's penis while it is in a not yet fully erect condition. In such applying step, the band is received about the penis and the shield associated therewith is turned towards and pressed against the subject's abdomen. Thereafter, the subject's penis is inserted into the vacuum erection chamber through its open end. While pressing the chamber open end into substantially vacuum sealing relationship with the tissue shield, the vacuum source is operated so as to evacuate the chamber for inducing an engorged condition of the subject's penis. Such engorged condition is captured with the cincture band while at the same time the tissue shield prevents any abdominal or scrotal tissue of the subject from being drawn into the vacuum chamber, all in accordance with the subject invention.

Those of ordinary skill in the art will better appreciate the features and aspects of such embodiments, methods, and others, upon review of the remainder of the specification.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended figures, in which.

Figure 4:
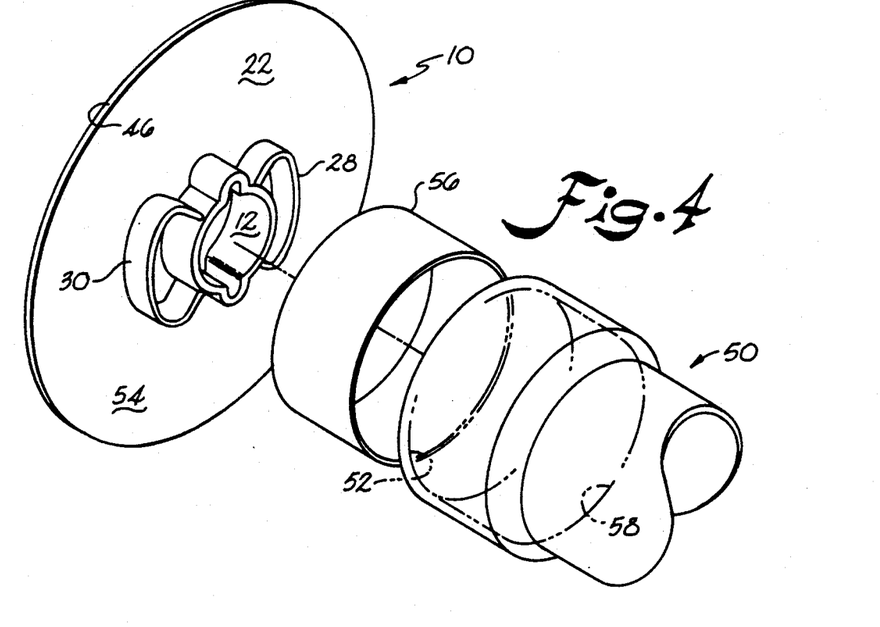
FIGS. 4 and 5 are perspective views of the first exemplary embodiment of present FIGS. 1 through 3, further illustrating present methodology associated with such improved cincturing device and vacuum erection devices and therapies, in accordance with the subject invention.
Figure 5:
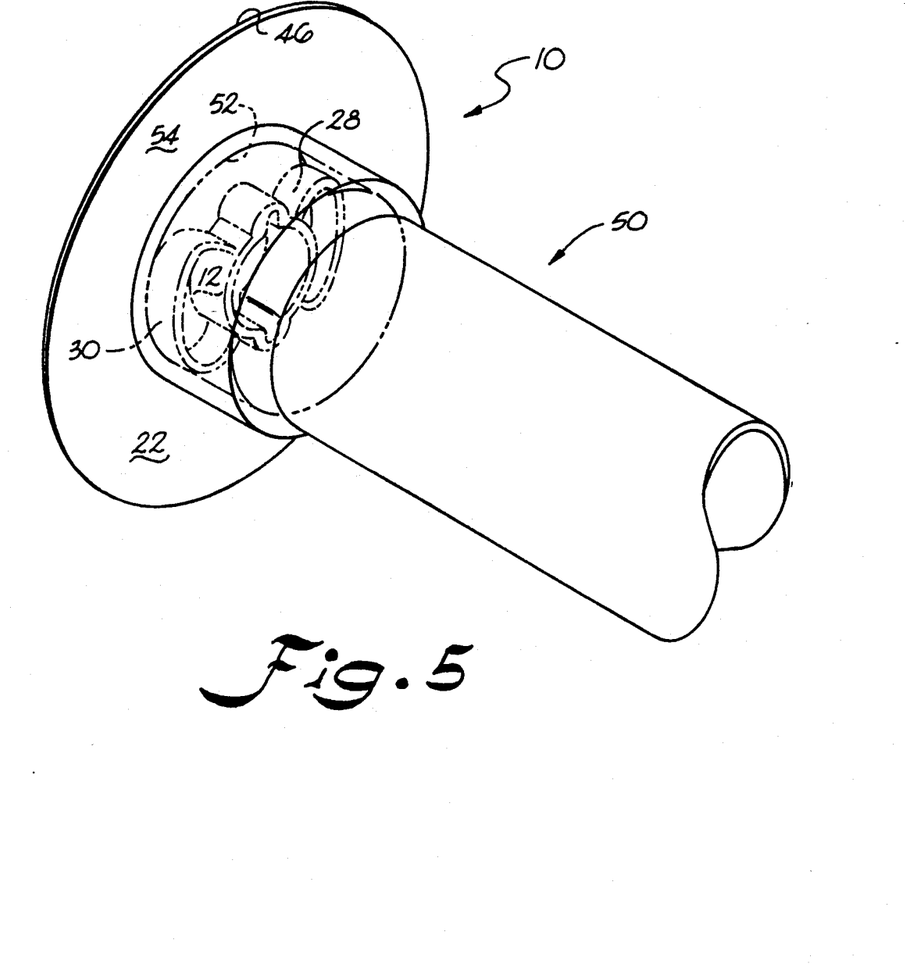
Figure 6:
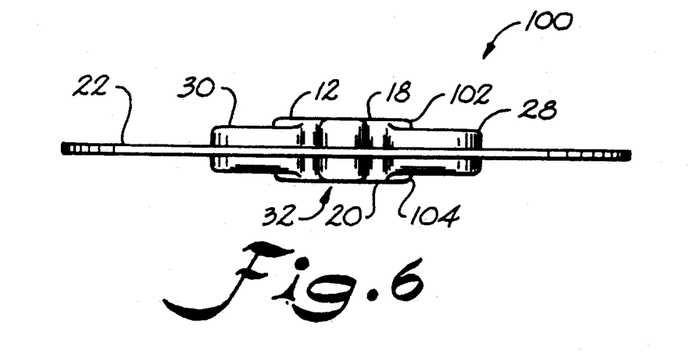
FIG. 6 is a side elevational view of a second exemplary embodiment of an improved cincturing device in accordance with the subject invention.
Figure 7:
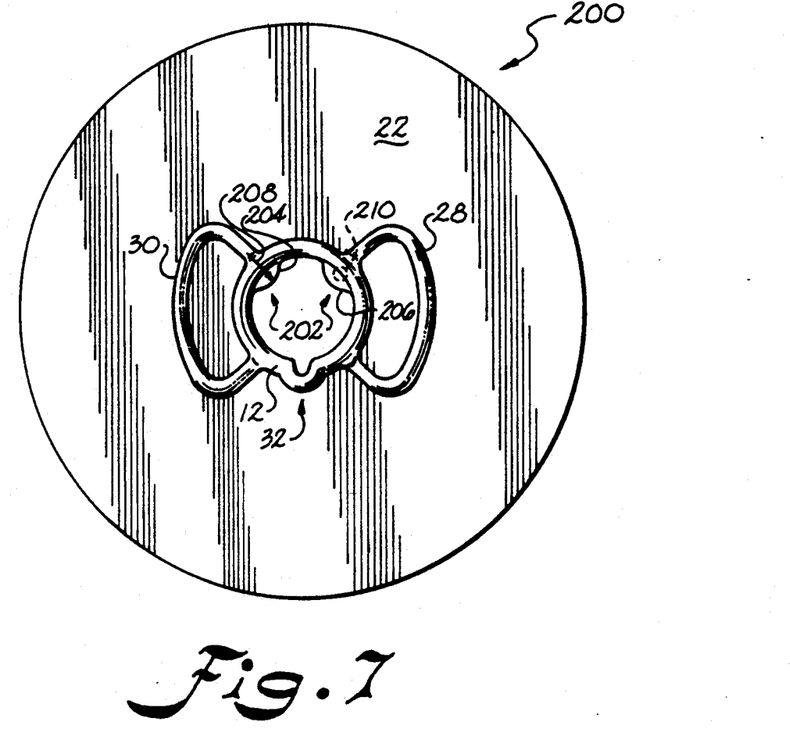
FIG. 7 is a top plan view of a third exemplary embodiment of an improved cincturing device in accordance with the subject invention.
Figure 8:
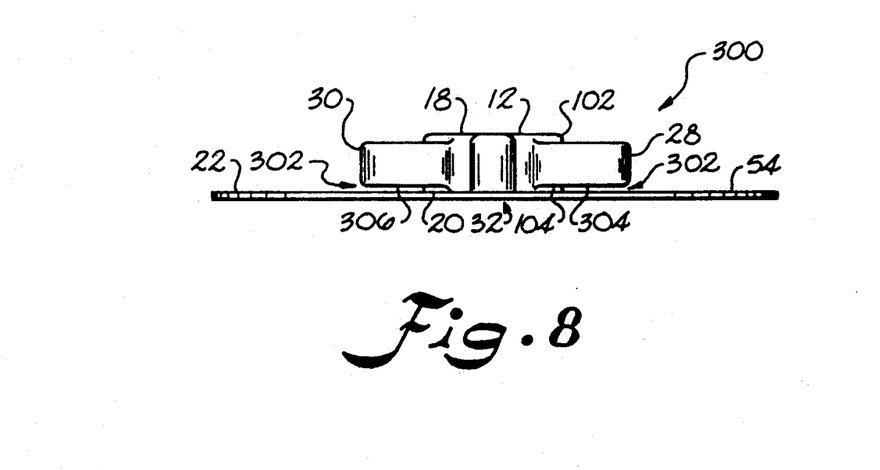
FIG. 8 is a side elevational view of a fourth exemplary embodiment of an improved cincturing device in accordance with the subject invention.

It is to be understood that the alternative embodiments represented by present FIGS. 6 through 8 may be likewise practiced with the methodology represented by present FIGS. 4 and 5 and as discussed in the remainder of this specification. Also, it is to be understood that the alternative features illustrated and represented by present FIGS. 6 through 8 may be variously incorporated into and practiced in different combinations comprising present different embodiments, even though all such possible combinations of features for a given embodiment may not be shown in a single illustration herewith.

Still further, it is to be understood that repeat use of reference characters throughout the present specification and appended drawings is intended to represent same or analogous features, elements, or steps of the subject invention.

DETAILED DESCRIPTION OF THE PREFERRED EMBODIMENTS

Figure 1:
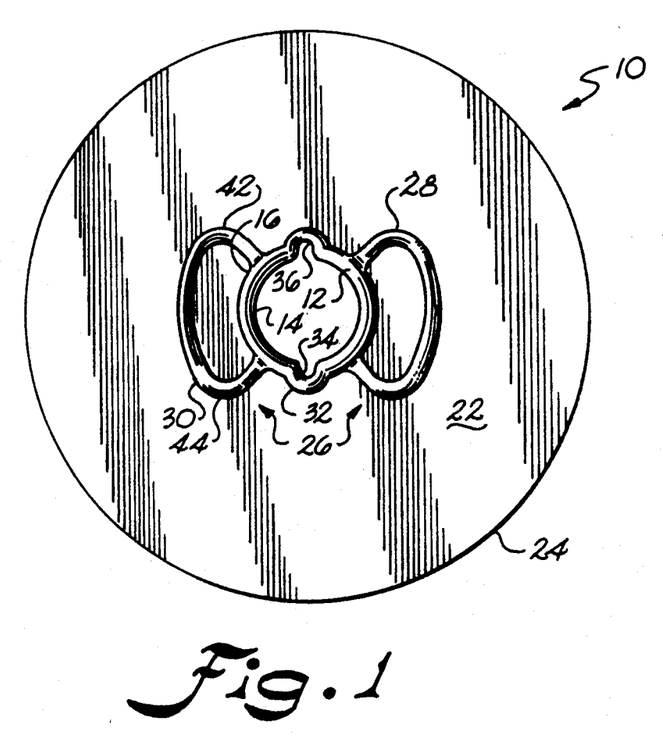
FIG. 1 is a top plan view of a first exemplary embodiment of an improved cincturing device in accordance with the subject invention.
Figure 2:
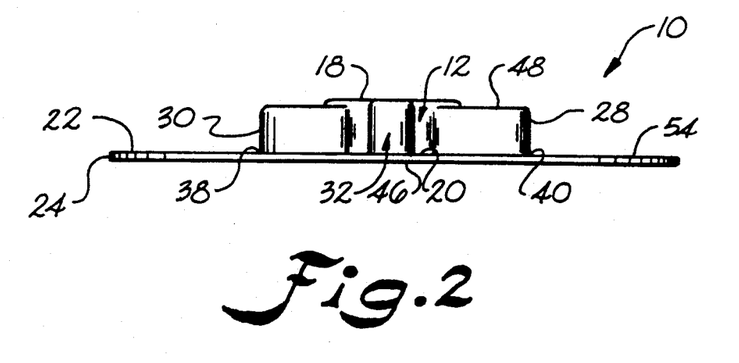
FIG. 2 is a side elevational view of the first exemplary embodiment shown in present FIG. 1.
Figure 3:
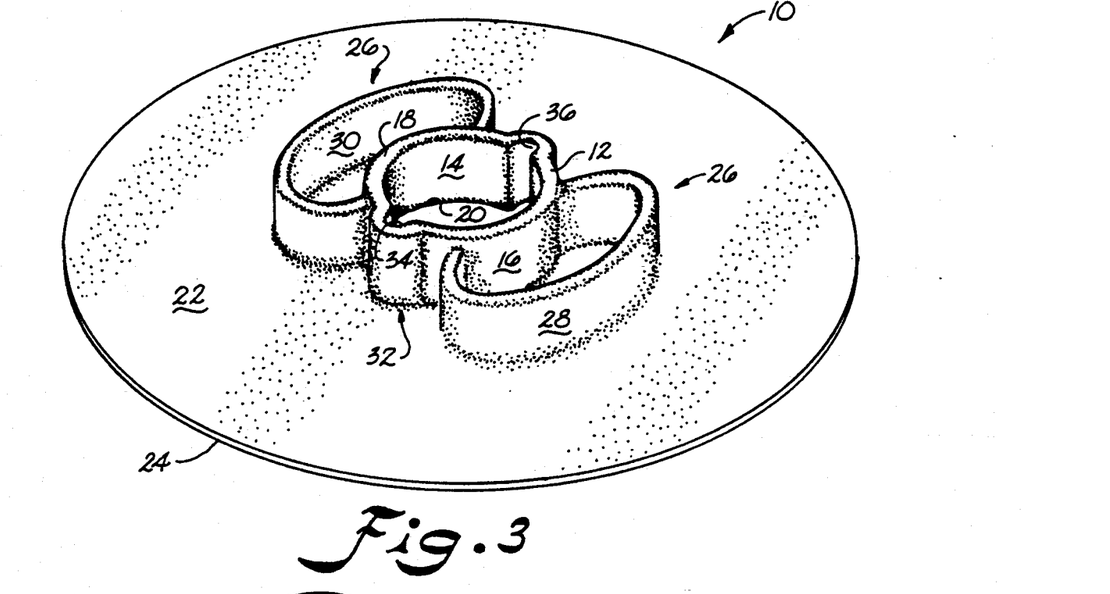
FIG. 3 is a perspective view of the first exemplary embodiment of present FIGS. 1 and 2.

The following discussion describes various presently preferred embodiments of the subject invention, with the intention that such description and embodiments are by way of example only, without limiting the broader aspects of the present apparatus and method. FIGS. 1 through 3 illustrate plan, side elevational, and perspective views, respectively, of a first embodiment of an improved cincturing device generally 10 in accordance with the subject invention. The stippling of FIG. 3 is intended to represent surface features.

Penile erection constriction device 10 is preferably comprised of elastic material, such as natural or synthetic rubbers or the like. Use of device 10 results in improved comfort and safety for a male subject so as to protect sensitive scrotal and abdominal tissue and enclosed sexual organs of the subject user during vacuum inducement of an engorged condition of the male sex organ, as described in greater detail hereinafter with collective reference to present FIGS. 1 through 3.

Improved cincturing device 10 preferably includes elastic ring means or an elastic cincture band generally 12 for retaining an engorged condition of a user's male sex organ by restricting the outward flow of blood therefrom. Elastic ring means 12 has an inside diameter 14 and a respective outside diameter 16. The inside diameter 14 may be of a predetermined size for initial receipt thereof about the base of a user's male sex organ. In other words, it is of an adequate unstretched initial inside diameter so as to facilitate application of band 12 to a subject's penis which is in a less than fully erect state.

The respective outside diameter 16 may also be of a predetermined size for receipt of the ring means 12 within the inside diameter of a vacuum erection chamber open receiving end, as discussed in greater detail below with reference to present FIGS. 4 and 5.

The inside diameter of cincture band 12 may fall in a range, for example, generally from about 0.7 to about 0.9 inches. An unstretched inside diameter of at least generally about 0.75 inches is an example of one preferred embodiment. An outside diameter 16 of generally less than about 2 inches is preferred so that the entire ring 12 may be received inside a typical vacuum chamber receiving end, which is generally at least about 2 inches (without any adapters inserted).

Other dimensions of cincture band 12 may comprise a range of specific dimensions. For example, the band wall thickness (i.e., the distance in a radially outward direction between inside diameter 14 and outside diameter 16) may fall generally in a range of from about 0.08 to about 0.12 inches. Cincture band 12 has two opposing axial direction sides generally 18 and 20 with a predetermined band axial thickness therebetween generally in a preferred range of from about 0.35 to about 0.55 inches.

Further included in device 10 in accordance with the subject invention is a flange means or tissue shield generally 22. As illustrated, such tissue shield 22 preferably is generally planar and preferably is generally of the same elastic material of which ring 12 is comprised so as to be integrally formed therewith or attached thereto. Flange means 22 may also comprise an annular shape which projects radially outward from ring means 12 a distance greater than the outside diameter of a vacuum erection chamber open receiving end. In general, for at least one presently preferred embodiment, tissue shield 22 is sufficiently large (whether specifically annularly shaped or not) for extending radially outward from band 12 at least about 1.5 inches in all directions from the center of such band.

In accordance with the subject invention, the tissue shield 22 is also made sufficiently rigid for preventing abdominal and scrotal tissue (i.e., skin) of a subject from being drawn into a vacuum erection chamber whenever an open end of such a chamber during its vacuum operation is applied to the shield with the shield received against the abdomen of a subject and with band 12 received about the root of the subject's penis and inside the vacuum erection chamber open end, as discussed below.

As further shown by the first embodiment 10 in accordance with the subject invention, the scrotal and abdominal tissue shield 22 preferably comprises a planar annular member which is integrally formed on one axial side, such as axial side 20, of cincture band 12. The tissue shield 22 may be of an annular nature such that it has an inside diameter generally coextensive with cincture band 12, which permits the male subject's penis to be inserted through shield 22 as well as band 12, as will be understood by those of ordinary skill in the art from the present disclosure without the necessity of specific anatomical representations. The outside diameter 24 of an annular configured tissue shield 22 is generally concentric with cincture band 12 and generally at least about 3 inches in diameter.

As represented by present FIGS. 1 through 3, additional features may be practiced in combinations constituting further present embodiments of the invention. For example, handle means generally 26 may be associated with elastic ring means 12 for improved user manipulation of constriction device 10. Again, preferably such handle means project a predetermined distance (radially outward from the center of ring 12) sized for receipt of the handle means within the inside diameter of a vacuum erection chamber open receiving end, as discussed below with reference to present FIGS. 4 and 5.

More specifically, such handle means 26 may comprise a pair of curved loop handles 28 and 30 preferably integrally formed with (or attached to) cincture band 12 and projecting radially outward therefrom in opposite directions about the circumference of such band 12. If an associated (or to be associated) vacuum erection chamber open receiving end has an inside diameter of at least about 2 inches, then each handle 28 and 30 preferably projects radially outward from the center of band 12 by generally less than 1 inch so that both the band 12 and the handles 28 and 30 can be received in such vacuum chamber open end during vacuum operations.

As represented in present FIGS. 1 through 3, such handle means 26 may further be attached to (or integrally formed with) tissue shield 22. Such an arrangement functions to supplement the rigidity and stability of tissue shield 22, thus further contributing to achieving the general objects stated above. Even when not so attached, handles in relatively close proximity to the tissue shield can contribute to the stability, and hence the relative rigidity, of flange means 22.

Still further, elastic penile erection constriction device generally 10 may further include urethra channel means generally 32 formed in elastic ring means 12 for receiving the urethra of a user's male sex organ whenever ring 12 is seated about such organ in proper circumferential and rotational relationship thereto. Such channel improves user seminal discharge during climactic expulsion (i.e., ejaculation). Hence, such alternative feature further contributes to the present objects of approximating natural experiences as best as possible, and with as little interruption or distraction as possible.

As represented in present FIGS. 1 through 3, such urethra channel means 32 may comprise at least one protruding channel 34 formed in a radially outward direction in the elastic ring means inside diameter 14. As one example of a preferred location, respective handle loops 28 and 30 may be centered respectively about 90 degrees from urethra cradle 34 about the circumference of band 12.

Urethra cradle 34 preferably has a depth of generally at least about 0.05 inches for axial alignment with and receipt of the user's urethra whenever band 12 is applied in a predetermined rotational relationship about the base of such penis. More preferably, such urethra channel depth is generally at least about 0.1 inches.

As still further shown in present FIGS. 1 through 3, urethra channel means 32 may optionally include a second protruding channel 36 also formed radially outwardly in ring inside diameter 14. The location of channel 36 is generally circumferentially opposite to that of the first protruding channel 34, and serves to further facilitate a desired positioning of device 10 on a male subject.

Either or both of urethra channels or cradles 34 and 36 (when present together or alone) preferably may be generally U-shaped, as illustrated. Such an arrangement particularly accommodates the user's urethra, though other shapes such as V-shaped or the like may be practiced in some present embodiments.

As shown by the figures thus far described, constriction device 10 preferably comprises an integrally associated construction of elastic material, though variously joined members could be practiced in some embodiments. Such elastic material may comprise materials as referenced above in the disclosures of the United States patents incorporated in this application by reference. As further specific examples, various polyisoprene compounds may be utilized, possibly with different characteristics associated for example with respective colors for the purpose of identifying to a user a given device 10 having specific materials characteristics. More specific characteristics for two specific examples are set forth in the following table.

TABLE I

| Characteristic | First Example | Second Example |
|---|---|---|
| Durometer, Shore | 28–33 | 28–33 |
| Tensile, PSI | 1300–2400 | 1500–2300 |
| Modulus, 100% PSI | 75–125 | 75–125 |
| Elongation, % | 1050–1350 | 1200–1450 |

In addition to the exemplary range of dimensions and characteristics noted above, other present features of device 10 may have dimensions which fall into specific ranges for some preferred embodiments. For example, the outside diameter 24 of tissue shield 22 for those embodiments thereof wherein such shield is generally circular, may have dimensions in a range of from about 3 to about 5 inches.

Dimensionally speaking, and with reference primarily to FIGS. 1 and 2, the following sets forth specific exemplary information for one presently preferred exemplary embodiment of an improved cincturing device generally 10 in accordance with the subject invention.

The outside diameter 24 of such flange means or tissue shield 22 is about 3.875 inches. The inside diameter 14 of cincture band 12 is about 0.75, inches. The distance between the bottom of the channels formed by the two opposing urethra cradles 34 and 36 is approximately 1 inch. The outside distance or radial projection of handle means 26 (i.e., the distance between points 38 and 40 of FIG. 2) is about 1.9 inches. As shown, the outside curvature of handles 28 and 30 preferably is concentric with the outside circular diameter 16 of ring 12, which means that the outside portions of handles 28 and 30 fit closely with the generally circular open end of the vacuum erection chamber so as to further stabilize the overall arrangement.

The top to bottom length of each handle 28 and 30 (i.e., the distance between points 42 and 44 of FIG. 1) is preferably about 1.125 inches. The ring depth or band axial thickness (i.e., the distance between opposing axial sides 18 and 20 of present FIG. 2) is about 0.425 inches. At the same time, the wall thickness of ring 12 (i.e., the radially outward distance between a point on inside diameter 14 and a point on outside diameter 16) is about 0.1 inches.

The axial direction thickness of tissue shield 22 (i.e., the distance between axial side 20 of disc 12 and opposing axial side 46 of tissue shield 22) is about 0.075 inches. At the same time, the axial direction thickness of the handles (i.e., the distance between handle axial side 48 and opposing axial side 20 of ring 12) is about 0.35 inches.

FIGS. 4 and 5 illustrate one example of present methodology in accordance with the subject invention, including providing an elastic cincturing device 10 in accordance with the subject invention and providing a generally elongated vacuum erection chamber generally 50 with an open end 52 for receiving a male subject's sex organ therethrough into the chamber. With respect to vacuum chamber 50 and associated features, the disclosure of commonly assigned and above-noted U.S. Pat. No. 4,856,498 is fully incorporated herein by reference. Such '498 patent includes a vacuum source which may be utilized for controllably evacuating the chamber 50.

The exemplary cincturing device 10 illustrated in conjunction with the presently discussed methodology includes an exemplary elastic cincture band 12 and an exemplary generally planar tissue shield 22. Both such features 12 and 22 incorporate and include characteristics of the subject invention as discussed above. Additional features, for example such as handles 28 and 30, may be optionally practiced.

Illustration of a male subject's anatomy is not required for a complete understanding of the present invention and is presently omitted from FIGS. 4 and 5 for greater clarity in illustrating and representing the following features.

FIG. 4 represents the position of cincture band 12 after it has been applied to the base of a male subject's penis with band 12 received about the penis. The term axial herein refers to the direction generally along the lengthwise or axial direction of the penis. An axial side 46 is opposite to axial side 54 of tissue shield 22. Axial side 46 of tissue shield 22 is turned towards and pressed against the male subject's abdomen, while axial side 54 thereof is turned towards the distal end of the user's penis (i.e., away from the abdomen). In general, such step of applying the cincturing band is conducted while the subject's penis is in a not yet fully erect condition, (i.e., either flaccid or semi-flaccid), which application is facilitated by the characteristics of the ring 12 and its inside diameter 14, as discussed above.

FIG. 4 further represents an adapter insert 56 which may be placed into the open receiving end 52 of chamber 50 and seated therein against a shoulder 58 or similar locating feature, all in accordance with and fully disclosed by U.S. Pat. No. 4,856,498. FIG. 4 also represents, in fact, a next step in accordance with the subject invention of inserting the subject's penis into the vacuum erection chamber 50 through the open end 52 thereof (and with adapter insert 56 being optionally utilized). Typically, such adapter would be fully seated in its intended position relative chamber 50 before the insertion step actually begins, but is shown in a separated position here for greater clarity in the illustration.

FIG. 5 represents the next progressive step in the present exemplary methodology, in which the chamber open end 52 is pressed into substantially vacuum sealing relationship with axial surface 54 of the tissue shield 22. Typically, vacuum chamber 50 may be comprised of optically transparent materials, such as plastics or the like, in which case anything inside of chamber 50 would continue to be visible. Such is particularly useful in order to monitor vacuum induced engorgement operations. In this instance, in accordance with features of the subject invention, ring 12 and any other elements such as handles 28 and 30 found on the distal side 54 of tissue shield 22 are of a predetermined size so as to be received inside chamber 50 through open end 52 thereof. Such features are shown in the illustration of present FIG. 5 in broken line illustration to represent their interior position relative chamber 50, though they would ordinarily still be visible whenever optically transparent material is utilized for such chamber.

Once the arrangement of FIG. 5 is established with the male subject's anatomy in place as described above, the vacuum source may be operated in accordance with present methodology so as to evacuate chamber 50, resulting in a vacuum induced engorged condition of the subject's penis. Such penile engorged condition is captured with the cincture band 12 as understood by those of ordinary skill in the art. At the same time, and further in accordance with the subject invention, it will be apparent from the present disclosure that tissue shield 22 operates as flange means for preventing any abdominal or scrotal tissue or other sexual anatomy of the male subject external to the abdomen from being drawn into vacuum chamber 50 through open end 52 thereof. Use of an adapter insert 56 is not represented in present FIG. 5 so as to illustrate the relatively close relationship for some embodiments of the subject invention between the outer curvature of handles 28 and 30 (whenever such handle means are utilized) and the inside curvature of open end 52.

It will be understood by those of ordinary skill in the art without further discussion that vacuum chamber 50 is removed from cincturing device 10 after a penile engorged condition is captured therewith, upon which the male subject is prepared in the desired sexually potent state.

It will be understood by those of ordinary skill in the art from the present disclosure that improved cincturing devices in accordance with different embodiments of the subject invention may be practiced in conjunction with present methodologies, such as the exemplary method described above with reference to present FIGS. 4 and 5. FIG. 6 represents a side elevational view of one such alternative exemplary embodiment, and comprises a second exemplary embodiment of an improved cincturing device generally 100 in accordance with this invention. Ring means 12 and opposing looped handles 28 and 30 may be practiced generally as described above, as is the case with reference to urethra channel means 32. However, instead of being located on one axial side of the ring (such as axial side 20), flange means or tissue shield 22 of device 100 are generally positioned between opposing axial sides 18 and 20 of ring means 12. More preferably, per the exemplary configuration of present FIG. 6, such flange means planar member 22 is situated generally about halfway (i.e., in a relatively medial position), between the opposing axial sides 18 and 20 of ring means 12.

In such exemplary FIG. 6 embodiment, flange means 22 are illustrated as being integrally associated with handles 28 and 30, though the handles could be formed or provided as unattached to the flange means 22 (though still attached to the outside diameter of ring means 12).

In addition, whenever handles 28 and 30 are relatively centered between opposing axial sides 18 and 20 of ring means 12, areas 102 and 104 of ring means 12 appear on respective axial sides of handles 28 and 30 to relatively project therefrom. As represented, preferably in each such instance, the resulting surfaces are slightly rounded so as to ensure no user discomfort from any exposed edges or the like.

FIG. 7 represents a top plan view of a third exemplary embodiment of an improved cincturing device generally 200 in accordance with the subject invention. In such embodiment, a ring 12 is again associated with an exemplary tissue shield 22, and may be further optionally provided with handles 28 and 30 and/or urethra channel means 32. However, the exemplary embodiment of present FIG. 7 illustrates still further alternative features comprising enhanced pressure means generally 202 formed in the elastic ring means 12 for relatively increasing radially inward pressure on the user's male sex organ at least at one circumferential location thereof.

More particularly, such enhanced pressure means generally 202 may include a pair of radially inward curved projections 204 and 206. Such projections have a predetermined radius of curvature which may encompass a range of values, which preferably is at least generally about 0.1 to about 0.15 inches. In one exemplary embodiment, a radius of curvature 208 of 0.187 inches is preferred.

Also preferred is that such pair of projections be situated in predetermined spaced circumferential locations on the elastic ring means 12 inside diameter 14. With such an arrangement, such as represented in present FIG. 7, the projections are positioned adjacent respective lateral generally dorsal venous process regions of a user's male sex organ, so as to provide specified restrictive forces thereto. By applying such specified or localized restrictive forces, greater user comfort may be obtained by relatively lessening the remaining radially inward compressive forces on the user's penis, for example, by making the inside diameter of ring 12 slightly larger than it would otherwise have been.

As further represented by dotted line generally circular illustration 210 of present FIG. 7, such projections 204 and 206 may define respective chambers therein and include relatively hardened elements received in such chambers so as to further relatively increase the radially inward pressure. Where projections 204 and 206 are integrally formed with the cincture band 12, they comprise the same elastic material as such band 12. In such instance, the relatively hardened element contained within chamber 210 may preferably include hardened plastics, such as ABS plastics or the like.

FIG. 8 represents a side elevational view of yet a fourth exemplary embodiment of an improved cincturing device generally 300 in accordance with the subject invention. Similar to the side elevational views of prior FIGS. 2 and 6 for exemplary devices 10 and 100, respectively, a ring 12 may be provided with a tissue shield 22, and optionally with handles 28 and 30 and/or a urethra channel means 32. In the FIG. 8 exemplary embodiment, tissue shield or flange means 22 is once again located so that one axial side 54 thereof is secured or attached to (or integrally formed with) an axial side 20 of ring means 12. Such an arrangement is similar in such respect to that of present FIG. 2 rather than that of present FIG. 6. However, the handle elements 28 and 30 are configured more like that of the exemplary embodiment of present FIG. 6 than that of FIG. 2.

More specifically, handles 28 and 30 are respectively centered between opposing axial sides 18 and 20 of ring means 12 and have an axial thickness less than that of ring means 12 so as to again create relatively projecting areas 102 and 104. However, while handles 28 and 30 are integrally formed with or otherwise attached to ring means 12, they are not in any way formed with or otherwise attached to flange means 22. Such an arrangement results in a gap 302 being formed between axial side 304 of handle 28 and axial side 54 of tissue shield 22 and between axial side 306 of handle 30 and axial side 54 of tissue shield 22. However, even with such an arrangement, handles 28 and 30 can provide additional relative rigidity and stability to flange means 22 by acting as a stop against or limit to dislocation of tissue shield 22 as it is drawn by a vacuum chamber 50 towards the distal side 18 of ring means 12.

It will be apparent to those of ordinary skill in the art from the present disclosure that the foregoing embodiments result in an improved cincturing device which facilitates application thereof to even a totally flaccid penis of a user, while subsequently protecting against potential vacuum intake of highly sensitive scrotal or abdominal tissue or other external male sexual organs or anatomy (apart from the penis which is intentionally introduced into the chamber 50). All of the foregoing embodiments of present apparatus and methodology contribute to improved user comfort and safety with vacuum erection devices and therapies, further contributing to achievement of present objects.

It will be further appreciated that modifications and variations may be practiced, including combinations of presently disclosed features which are not necessarily illustrated in such combinations by a single figure herewith. For example, the enhanced pressure means features generally 202 of present FIG. 7 may be incorporated into the present embodiment of device 10 shown in present FIGS. 1 through 5 (perhaps with omission of second urethra channel 36 therein). Other combinations not presently illustrated may likewise be practiced, including use of all devices 10, 100, 200, 300, and their equivalents interchangeably in conjunction with the methodology discussed in conjunction with present FIGS. 4 and 5.

Yet further, additional features may be practiced or otherwise modified. For example, the presently illustrated handles 28 and 30 may be placed in different relative locations, provided with different dimensions, or provided with different shapes. For example, the handles shown in commonly assigned U.S. Pat. Nos. Des. 317,504 and Des. 317,505, fully incorporated herein by reference, may be utilized.

It should be further understood by those of ordinary skill in the art that the foregoing presently preferred embodiments are exemplary only, and that the attendant description thereof is likewise by way of words of example rather than words of limitation, and their use do not preclude inclusion of such modifications, variations, and/or additions to the present invention (apparatus and method) as would be readily apparent to one of ordinary skill in the art, the scope of the present invention being set forth in the appended claims.

What is claimed is:

1. An elastic penile erection constriction device for improved comfort and safety during use of a vacuum erection chamber having an open receiving end for receipt of a user's male sex organ, such end being formed with predetermined, inside and outside diameters, said device comprising:

elastic ring means for retaining an engorged condition of a user's male sex organ by restricting the outward flow of blood therefrom, said elastic ring means having respective inside and outside diameters, including a predetermined inside diameter sized for initial receipt thereof about the base of a user's male sex organ and a predetermined outside diameter sized for receipt of said ring means within the inside diameter of the vacuum erection chamber open receiving end;

handle means associated with said elastic ring means for user manipulation of said constriction device, and projecting from said ring means a predetermined distance sized for receipt of said handle means within the inside diameter of the vacuum erection chamber open receiving end; and flange means associated with said elastic ring means and projecting radially outward therefrom a distance greater than the outside diameter of the vacuum erection chamber open receiving end for preventing the ingress of the user's scrotal and abdominal tissue into such receiving end during vacuum operations of the vacuum erection chamber, whenever said constriction device is seated about the base of his male sex organ.

2. An elastic penile erection constriction device as in claim 1, further including urethra channel means formed in said elastic ring means for receiving the urethra of the user's male sex organ for improved user seminal, discharge during climactic expulsion.

3. An elastic penile erection constriction device as in claim 2, wherein said urethra channel means comprises at least one protruding channel formed in a radially outward direction in said elastic ring means inside diameter.

4. An elastic penile erection constriction device as in claim 3, wherein said urethra channel means further includes a second, protruding channel formed radially outwardly in said elastic ring means inside diameter in a circumferential location thereof generally opposite to that of said at least one protruding channel.

5. An elastic penile erection constriction device as in claim 1, further including enhanced pressure means formed in said elastic ring means for relatively increasing radially inward pressure on the user's male sex organ at least at one circumferential location thereof.

6. An elastic penile erection constriction device as in claim 5, wherein said enhanced pressure means includes a pair of radially inward curved projections having a predetermined radius of curvature and situated in predetermined spaced circumferential ,locations on said elastic ring means inside diameter so as to be positioned adjacent respective lateral generally dorsal venous process regions of a user's male sex organ.

7. An elastic penile erection constriction device as in claim 6, further including:

a generally U-shaped urethra receiving channel formed in a radially outward direction in a predetermined circumferential location of said elastic ring means inside diameter, said channel having a depth of generally at least about 0.1 inches; and wherein said projections have a radius of curvature of generally at least about 0.15 inches.

8. An elastic penile erection constriction device as in claim 1, wherein said constriction device comprises an integrally associated construction of elastic material.

9. An elastic penile erection constriction device as in claim 18 wherein said handle means comprise a pair of loops attached to said ring means outside diameter on relatively opposite sides thereof.

10. An elastic penile erection constriction device as in claim 1, wherein:

said ring means have opposing axial sides with a predetermined thickness therebetween; and wherein said flange means are integrally associated with one of said ring means axial sides.

11. An elastic penile erection constriction device as in claim 10, wherein at least a portion of said flange means is integrally associated with at least a portion of said handle means.

12. An elastic penile erection constriction device as in claim 1, wherein:

said ring means have opposing axial sides with a predetermined thickness therebetween; and said flange means comprise a generally planar member integrally associated with said elastic ring means outside diameter generally positioned between said opposing axial sides of said ring means.

13. An elastic penile erection constriction device as in claim 12, wherein said flange means planar member is situated generally about halfway between said opposing axial sides of said ring means.

14. An elastic penile erection constriction device as in claim 12, wherein said handle means are integrally associated with said flange means.

15. An elastic penile erection constriction device as in claim 1, wherein said elastic ring means inside diameter is generally at least about 0.7 inches, and wherein said flange means comprises a generally planar and annular member having an inside diameter matching that of said elastic ring means and an outside diameter generally in a range of from about 3 to about 5 inches.

16. Apparatus for cincturing an engorged condition of a user's penis for improved user male potency and for protecting sensitive scrotal and abdominal tissue of the user during vacuum inducement of such penile engorged condition, said apparatus comprising:

a cincture band of elastic material having an inside diameter of generally about 0.7 to about 0.9 inches, a band wall thickness of generally about 0.08 to about 0.12 inches, and a band axial thickness of about 0.35 to about 0.55 inches;

a urethra cradle formed in a radially outward direction in a predetermined circumferential location in said cincture band inside diameter, and having a depth of generally at least about 0.05 inches for axial alignment with and receipt of the user's urethra whenever said cincture band is applied in a predetermined rotational relationship about the base of a user's penis;

a pair of curved loop handles integrally formed with said cincture band and projecting radially outward from said cincture band in opposite directions centered respectively about 90 degrees from said urethra cradle about the circumference of said band, each handle projecting radially outward generally less than 1 inch from the center of said cincture band so that said band and said handles can be received in an open end of a vacuum erection chamber having an open end inside diameter of generally at least about 2 inches; and a scrotal and abdominal tissue shield comprising a planar annular member integrally formed on one axial side of said cincture band so as to be received against the abdomen of a user whenever said cincture band is applied to the base of a user's penis, said annular member having an inside diameter generally coextensive with said cincture band and an outside diameter generally concentric with said cincture band and generally at least about 3 inches in diameter, so as to shield the user's abdominal and scrotal tissue from vacuum forces applied to the user's penis whenever an operating vacuum erection chamber is applied to a user's penis with the chamber open end pressed against the user's abdomen with said tissue shield interposed between such abdomen and such chamber open end.

17. Apparatus as in claim 16, wherein said urethra cradle is generally U-shaped and has a depth of at least about 0.1 inches.

18. Apparatus as in claim 16, wherein said handles are interconnected with at least one axial side of said tissue shield so as to increase relative rigidity and stability of said shield, and said tissue shield outside diameter is generally in a range of from about 3 to about 5 inches.

19. Apparatus as in claim 16, further including a pair of curved radially inward projections formed at respective lateral dorsal positions on said cincture band inside diameter for relatively increasing radially inward pressure to corresponding respective lateral dorsal locations on the user's penis.

20. Apparatus as in claim 19, wherein said projections are integrally formed with said cincture band and comprise said elastic material thereof, and further wherein said projections define respective chambers therein and include relatively hardened elements received in said chambers so as to further relatively increase said radially inward pressure.

21. Apparatus as in claim 16, further including vacuum chamber means for selectively inducing an engorged condition of the user's penis by application of a vacuum force thereto with said cincture band received about the user's penis and said tissue shield interposed between the user's abdomen and said vacuum chamber means.

22. An improved cincturing device for augmenting male potency and protecting abdominal and scrotal tissue during vacuum erection therapy of a male subject, said device comprising an elastic cincture band to be received about the root of a subject's penis and having an unstretched inside diameter of at least generally about 0.75 inches to facilitate application of said band to a subject's penis which is in a less than fully erect state, and a generally planar tissue shield of generally elastic material having an annular opening corresponding to that of said band, said shield being attached to said band and being sufficiently large for extending radially outward from said band at least about 1.5 inches in all directions from the center of said band, and said shield being sufficiently rigid for preventing abdominal and scrotal tissue of a subject from being drawn into a vacuum erection chamber whenever an open end of such a chamber during its vacuum operation is applied to said shield with said shield received against the abdomen of a subject and with said band received about the root of the subject's penis and inside the vacuum erection chamber open end.

23. An improved cincturing device as in claim 22, further including handle means attached to said elastic band for manipulating said cincturing device.

24. An improved cincturing device as in claim 23, wherein said handle means comprise a pair of loops integrally formed with the outside diameter of said elastic band and having a total outside dimension of generally less than 2 inches so as to fit inside the open receiving end of a vacuum erection chamber having an open receiving end inside diameter of generally at least about 2 inches.

25. An improved cincturing device as in claim 23, wherein said handle means are further attached to said tissue shield so as to supplement the rigidity and stability thereof.

26. An improved cincturing device as in claim 22, wherein said band has a predetermined axial width, and said tissue shield is attached to said band along one axial side of said band.

27. An improved cincturing device as in claim 26, wherein said tissue shield has a generally circular outside diameter in a range of from about 3 to about 5 inches.

28. An improved cincturing device as in claim 22, wherein said band has a predetermined axial width, and said tissue shield is attached to said band about a medial circumferential location thereof.

29. An improved cincturing device as in claim 22, further including urethra cradle means formed in said elastic cincture band inside diameter for receiving the subject's urethra whenever said band is correspondingly seated about the subject's penis.

30. An improved cincturing device as in claim 22, further including enhanced pressure means formed in said elastic cincture band inside diameter for relatively increasing radially inward pressure on the user's penis at least at one circumferential location thereon.

31. A method of augmenting the potency of a male subject with vacuum erection therapy while protecting abdominal and scrotal tissue of the male subject, said method including:

providing an elastic cincture band having an unstretched inside diameter of at least generally about 0.75 inches, with a generally planar tissue shield of generally elastic material having an annular opening corresponding to that of said band, and with said shield being attached to said band and having a predetermined size so as to extend radially outward from said band at least about 1.5 inches in all directions from the center of said band, and said shield having a predetermined rigidity so as to prevent abdominal and scrotal tissue of a subject from being drawn from one side of said shield to another by a vacuum applied to the subject's penis;

providing a generally elongated vacuum erection chamber with an open end for receiving a subject's penis therethrough into said chamber and a vacuum source for controllably evacuating said chamber;

applying said cincture band to the base of a subject's penis with said band received about the penis and with said shield turned towards and pressed against the subject's abdomen, said applying step being performed while the subject's penis is in a not yet fully erect condition;

inserting the subject's penis into said vacuum erection chamber through said open end thereof; and pressing said chamber open end into substantially vacuum sealing relationship with said tissue shield while operating said vacuum source to evacuate said chamber so as to induce an engorged condition of the subject's penis, which penile engorged condition is captured with said cincture band while said tissue shield prevents any abdominal or scrotal tissue of the subject from being drawn into said vacuum chamber.

32. A method as in claim 31, further including providing handles attached to said elastic band for manipulation thereof.

33. A method as in claim 32, further including forming said handles so as to have a total dimension smaller than the inside diameter of said vacuum erection chamber open end so that said handles are received inside of said chamber open end during said pressing and evacuating steps.

34. A method as in claim 32, further including attaching said handles to said tissue shield so as to supplement the rigidity and stability thereof.

35. A method as in claim 31, further including:
providing said band with a predetermined axial width; and
attaching said tissue shield to one axial side of said band.

36. A method as in claim 35, further including providing said tissue shield with a generally circular outside diameter in a range of from about 3 to about 5 inches.

37. A method as in claim 31, further including:
providing said band with a predetermined axial width; and
attaching said tissue shield about a medial circumferential location of said band.

38. A method as in claim 31, further including providing urethra cradle means formed in said elastic cincture band inside diameter for receiving the subject's urethra whenever said band is correspondingly seated about the subject's penis.

39. A method as in claim 31, further including providing enhanced pressure means formed in said elastic cincture band inside diameter for relatively increasing radially inward pressure on the user's penis at least at one circumferential location thereon.

* * * * *